United States Patent [19]
Chiarenza et al.

[11] 4,175,565
[45] Nov. 27, 1979

[54] METHOD AND APPARATUS FOR STIMULATING OSTEOGENIC ACTIVITY IN BONE STRUCTURE ADJACENT A DENTAL IMPLANT

[75] Inventors: Angelo R. Chiarenza, Islip; Charles M. Weiss, New York, both of N.Y.

[73] Assignee: Oratronics, Inc., New York, N.Y.

[21] Appl. No.: 808,724

[22] Filed: Jun. 22, 1977

[51] Int. Cl.² ............................................. A61N 1/20
[52] U.S. Cl. .................................... 433/32; 433/174; 433/176; 128/419 F; 128/785; 128/787
[58] Field of Search ............. 128/1, 10 A; 32/1, 10 A

[56] References Cited
U.S. PATENT DOCUMENTS

| 535,905 | 3/1895 | Horton et al. ....................... 128/409 |
| 2,121,875 | 6/1938 | Kruse et al. ...................... 128/362 X |
| 2,276,623 | 3/1942 | Meiman ............................ 128/409 X |
| 3,386,169 | 1/1968 | Scialom ................................. 32/10 A |
| 3,645,260 | 2/1972 | Cinotti et al. ..................... 128/172.1 |
| 3,837,080 | 9/1974 | Pasqualini ............................ 32/10 A |
| 3,842,841 | 10/1974 | Brighton et al. .................. 128/419 F |
| 3,955,583 | 5/1976 | Horauf ............................... 128/420 R |
| 4,019,510 | 4/1977 | Ellis .................................... 128/172.1 |
| 4,027,393 | 6/1977 | Ellis et al. ............................. 32/10 A |

FOREIGN PATENT DOCUMENTS 60500 3/1975 Australia .............................. 128/419 F

OTHER PUBLICATIONS

Braden et al., "Electrical . . . Dental Hard Tissues", Nature, vol. 211, Dec. 31, 1966, pp. 1565–1566.

Primary Examiner—Lee S. Cohen
Attorney, Agent, or Firm—James & Franklin

[57] ABSTRACT

An electroconductive dental implant is permanently imbedded in the jawbone of the subject, with a portion thereof extending into the oral cavity which is connected to a current source to act as a cathode. A second electroconductive electrode is non-permanently affixed to the skin of the subject, preferably at the ear, and connected to the source to act as an anode. The direct current applied to the implant and the electrode is preferably regulated so as to maintain a substantially constant current level throughout the application thereof. A continuous current, preferably of 200 microamperes or less is applied intermittently for relatively short periods not exceeding approximately one hour in duration. In this manner, osteogenic activity in the bone structure adjacent to the contours of the dental implant is stimulated in order to increase the rate of the normal healing process.

28 Claims, 5 Drawing Figures

METHOD AND APPARATUS FOR STIMULATING OSTEOGENIC ACTIVITY IN BONE STRUCTURE ADJACENT A DENTAL IMPLANT

The present invention relates to dental implantology and, in particular, to a method and apparatus for stimulating osteogenic activity in bone structure adjacent to the contours of a dental implant.

It is well known that certain crystalline materials, when mechanically deformed, develop an electric charge which is proportional to the degree of their deformation. This physical phenomenan has been the subject of considerable research relating to the stimulation of osteogenic activity by the application of an electrical stimulus to bone. Increased osteogenic activity and increased rates of the normal healing process have been reported by several investigators studying this phenomenan.

It is known (see Brighton et al, U.S. Pat. No. 3,842,841) that direct current of a given magnitude applied between a cathode inserted into a fracture or site of bone defect and an anode affixed to the skin near the implantation site will promote bone fracture healing. The method disclosed by Brighton et al. requires that the electrodes be percutaneously mounted at the fracture site, i.e. have one portion thereof imbedded within the body of the subject at a point adjacent the fracture site and another portion, electrically connected to the imbedded portion, extending beyond the skin such that it can be connected to the direct current source.

In this method, the current is applied continuously over long periods of time, for example weeks or months. However, the percutaneous implantation of electrodes for long term continuous application of direct current to bone is clinically unacceptable for use in dentistry as it is in other areas of medical activity because it is difficult to maintain the skin at the point of emergence of percutaneous electrodes viable and free from infection. Further, the formation of infected fistulous tracks and subsequent treatment and scar formation in the skin of the face, neck or other areas of the body would contra-indicate the use of such a method in most cases. Moreover, the introduction of electrodes in the oral cavity with connections passing through the opening of the mouth, for any protracted period of time, is likewise impractical because of the discomfort caused thereby.

In order to overcome the problems associated with percutaneous electrodes Werner Kraus in U.S. Pat. No. 3,783,880 issued Jan. 8, 1974, describes a method for aiding formation of bone forming material by placing two electrodes in spaced areas on opposite sides of the region of a bone fracture and applying an alternating electrical potential difference across the electrodes of a specified frequency and current density. In this patent, a rod-like magnetic core pickup arrangement is imbedded within the subject along with permanently inserted electrodes and an AC signal generator is positioned externally at a point adjacent the fracture and is utilized to apply an alternating current on the coil.

This method has, however, been found to be unsuitable because experiments clearly indicate that while bone formation is enhanced in the area of the electrode acting as the cathode, the bone material deteriorates adjacent the area of the electrode acting as the anode. Thus, the application of an alternating current to the electrodes does not produce optimum results. Thus, while the desirability of applying a direct current to the electrodes is known, this is obviously not possible with the method described by Kraus because the inaccessibility of the electrodes requires inductive coupling, between the electrode and the source, only possible through the use of alternating current.

Therefore, while the beneficial effects of the stimulation of osteogenic activity through the application of direct current to the bone by means of electrodes implanted in the bone have been amply demonstrated, there has been no practical clinical method developed for the utilization of this technique because of the undesirability of utilizing percutaneous electrodes over long periods of time due to the presence of infection at the skin around the electrode site, as well as the impracticability of having a patient with protruding electrodes connected to a power source over long periods of time.

The environment in the oral cavity is, however, substantially different from that of other portions of the body. For this reaason, it has been possible to utilize dental implants as electrodes to promote bone healing through the application of direct cement. Such implants, for example, are of the types described in U.S. Pat. No. 3,729,825 to Linkow et al., issued May 1, 1973, entitled "Improved Oral Implants"; U.S. Pat. No. 3,851,393 to Weiss et al., issued Dec. 3, 1974, entitled "Improved Oral Implant"; U.S. Pat. No. 3,849,888 to Linkow, issued Nov. 26, 1974, entitled "Bone Adapting Tissue Packing Post System"; and Application Ser. No. 556,456 of Charles M. Weiss et al., filed Mar. 7, 1975, entitled "Improved Threaded Self-Tapping Endodontic Stabilizer". These implants are designed with a first portion which is adapted to be imbedded into the patient's jawbone at the ridge crest and a relatively massive head portion which permanently extends into the oral cavity from the first portion and serves as a support upon which an artificial tooth structure can be mounted.

This insertion technique for blade type implants comprises incising the fibromuscular tissue at the ridge crest along the endendulous span involved, and reflecting that tissue away to expose the bone. The cortical layer of the alveolar crest is then grooved to a shallow depth and the blade portion of the implant is tapped to the desired depth into the bone. The tissue is then sutured.

The portion of the implant imbedded in the bone, if of the blade type, is preferably provided with open vents to allow for a substantial regeneration of the bone therethrough, thereby providing greatly increased retention after healing and bone growth. Because these implants are generally metallic in nature, they are electroconductive and the fact that they are implanted with a portion thereof extending into the oval cavity permits access thereto prior to the installation of a false tooth thereon and, thus, such implants are suitable during this period for use as an electrode in order to stimulate growth of bone adjacent the imbedded portion thereof.

It should be noted that while the term "dental implant" is utilized throughout the specification, this term is used in its broadest aspect, not only to refer to blade-type implants, discussed above, whether of the vented or unvented type, but also to include pin implants, both smooth and threaded, screw implants and endodontic stabilizers (externally threaded posts or non-threaded pins which are insertable into the bone through the root of a tooth) and any other electroconductive element designed for use within the oral cavity wherein a portion thereof is embedded in bone and a second portion thereof extends into the oral cavity to provide access thereto.

It has been experimentally determined that such dental implants can be utilized to stimulate osteogenic activity if direct current is applied thereto for intermittent periods, as well as a single protracted period. The present has formed the basis for a clinically acceptable method for increasing the noraml healing rate of bone structure by intermittent application of current for relatively short periods in duration.

It is, therefore, a prime object of the present invention to provide a method and apparatus for stimulating osteogenic activity in bone structure adjacent a dental implant in a clinically acceptable manner by utilizing a permanently imbedded dental implant a portion of which extends into the oral cavity as an electrode.

It is another object of the present invention to provide a method and apparatus for stimulating osteogenic activity in bone structure adjacent a dental implant through the use of an external non-permanently affixed anode located on some other portion of the subject's body spaced from the dental implant.

It is another object of the present invention to provide a method and apparatus of stimulating osteogenic activity in bone structure adjacent a dental implant through the application of a direct current to the bone during intermittent periods of relatively short duration.

It is a further object of the present invention to provide a method and apparatus of stimulating osteogenic activity in bone structure adjacent a dental implant by regulating the direct current to maintain a substantially constant current level throughout the application thereof.

In accordance with the present invention, the method of stimulating osteogenic activity in bone structure adjacent the contours of a dental implant requires the use of an electroconductive dental implant permanently imbedded in the jawbone and extending into the oral cavity. A second non-permanently affixed electroconductive electrode is placed on the skin of the subject at a part of the subject's body spaced from the dental implant, preferably on the ear. A direct current is applied to the implant and the electrode, the implant acting as a cathode and the electrode acting as an anode. The current is regulated to maintain a substantially constant current level throughout the application thereof. The direct current is preferably applied intermittently for relatively short periods of time, for instance, for the duration of up to approximately an hour, three times a week. The current is preferably 200 or less and acceptable results have been demonstrated with direct currents of 20, 40 and 100 microamperes, respectively.

The apparatus utilized in carrying out this method includes a direct current generator having means for regulating the level of current output to maintain same at a constant value. This current generator utilizes a voltage source, either in the form of batteries or a transformer and rectifier combination which is connected to the electrodes, the output circuit of a transistor and a resistance, which may be varied to set the desired current level. A second portion of the circuit, connected to the first portion, maintains the preset potential difference across the resistor such that the current flow between the electrodes is constant, regardless of variations in the resistance along the current path between the electrodes, which resistance varies appreciably during the treatment. In this manner, the current applied to the electrodes is kept at a substantially constant level throughout the application thereof, an important factor in promoting acceptable clinical results.

The current generator is preferably fashioned with a plurality of electrically independent current outputs, such that a plurality of bone sites can be electrically stimulated simultaneously. Each output can be independently set to generate a predetermined current level and the circuit is designed to maintain the set current level throughout the application of the current, independent of the functioning of the other portions of the current generator.

To the accomplishment of the above, and to such other objects as may hereinafter appear, the present invention relates to method and apparatus for stimulating osteogenic activity in bone structure adjacent the contours of a dental implant, as set forth in the annexed claims and described in detail in the specification, taken together with the accompanying drawings, wherein like numerals refer to like parts and in which:

Figure 1:
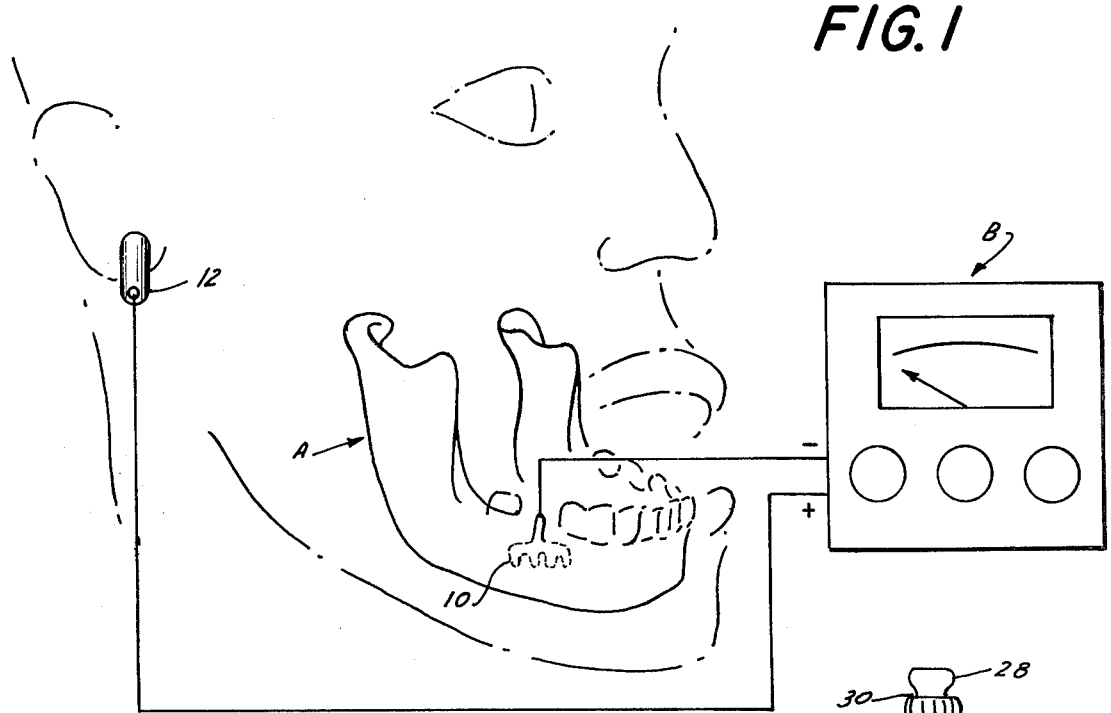
FIG. 1 is a partial cutaway view of a subject during treatment in accordance with the method of the present invention, the pertinent portion of the subject's oral cavity being exposed.
Figure 2:
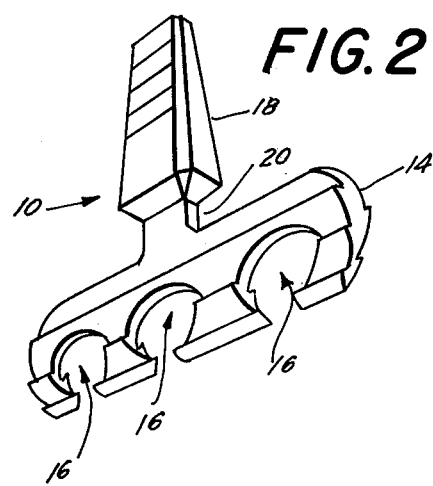
FIG. 2 is an elevational view of a blade-type dental implant of the type usable as an electrode in the present invention.

FIG. 1 is a schematic representation of a subject during treatment in accordance with the present method showing a portion of the subject's jawbone wherein a dental implant of the blade type, as shown in detail in FIG. 2, has been imbedded. The imbedding of the blade type implant is accomplished in accordance with well-known oral surgical techniques which are described in detail in the literature. The implant is operably connected to the negative side of the output circuit of a direct current generator, generally designated B, so as to act as a cathode. A second electrode 12, the particular structure of which forms no portion of the present invention, is connected to the positive side of the output circuit of current generator B so as to act as an anode. Anode 12 can be placed on the skin of the subject at any convenient location in the vicinity of the oral cavity. Preferably, anode 12 is placed on the earlobe of the subject.

Because of the unique environment of the oral cavity, it is possible to permanently imbed in the jawbone an electroconductive dental implant a portion of which extends into the oral cavity and still prevent infection or disruption of the surrounding tissue. This has been amply demonstrated by the use of blade-type implants, threaded pin implants and bone screws internationally in recent years. Thus, it is possible, to maintain a permanently imbedded bone implant a portion of which extends into the oral cavity for long periods of time in a medically accepted fashion. Because of this unique medical situation, it is possible to utilize the dental implant as an electrode to stimulate osteogenic activity in bone structure adjacent the imbedded portion of the implant to increase the rate of the normal healing process of the bone to conform with the contours of the imbedded portion of the implant.

Experimentation is currently being conducted to determine the optimum level of direct current to be applied to the electrodes in order to obtain the maximum stimulation of osteogenic activity in the bone. However, it is presently considered preferable to utilize direct current of 200 microamperes or less, noting specifically that currents of 100 microamperes, 40 microamperes and 20 microamperes, respectively, have demonstrated satisfactory results when applied for periods of less than one hour in duration, several times weekly, until the healing process has taken place.

From a treatment point of view, it is highly preferable that the direct current be applied intermittently for periods of relatively short duration as opposed to continuously over long periods of time because of patient comfort. Since at least one electrical connection must extend from the mouth of the patient to the current generator, it is a practical requirement of this method of treatment that the current be applied for relatively short periods of time so as not to produce undue patient discomfort. In addition, it is important to select a magnitude of current low enough so that the application thereof causes minimum patient discomfort and at the same time achieves acceptable clinical results.

Obviously, it is an object of any medical treatment to perform same in a manner which incurs as little patient discomfort as is possible. For this reason, the present invention is considered to be of paramount importance as it is the first treatment method of its kind wherein the duration of treatment and the current applied are calculated not only to achieve optimum results, but also to eliminate patient discomfort.

The electrical resistance which is present between the implant 10 and electrode 12 along the current path through the body of the subject will vary substantially during the period of application of the current. It has been determined experimentally that the value of the resistance along this path increases rapidly a short time after the application of the current. Thus, if the direct current generator B does not have incorporated therein some means of maintaining a substantially constant current across its output, the current supply to the electrodes will decrease rapidly a short time after the commencement of application thereof due to the increasing resistance along the current path through the body. This decrease in the applied current magnitude will significantly increase the required duration of the treatment and, thus, some means for automatically maintaining the applied current magnitude at the preset level, regardless of variations in the resistance of the current path through the body, is highly preferable.

Figure 3:
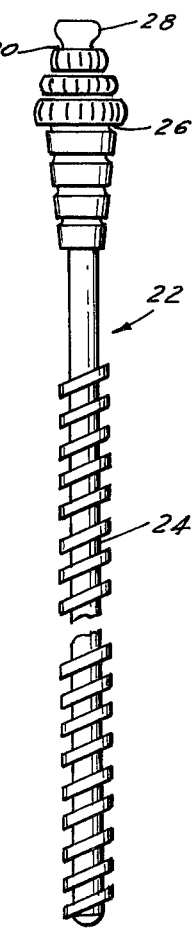
FIG. 3 is an elevational view of an endodontic stabilizer of the type usable as an electrode in the present invention.

FIGS. 2 and 3 illustrate a blade-type dental implant and an endodontic stabilizer, respectively, representative of the types of dental implants which are utilizable as electrodes in the method of the present invention. It should be understood that the implants illustrated in FIGS. 2 and 3 are merely representative of a large number of different structures which could be utilized as a cathode in the method disclosed herein. The particular structure of the implant plays no part in the present invention and, for purposes of the present invention, the only critical structural aspects of the implant are that the implant be made of electroconductive material and that it have two portions, one of which is designed to be imbedded in the bone and a second portion, electrically and physically connected to the first portion, which is designed to extend into the oral cavity to permit operable connection to the current generator.

FIG. 2 shows a blade-type dental implant 10 having a blade portion 14 with a series of openings 16 therein. When considered in cross-section, the blade portion 14 is provided with a series of bone engaging teeth along each side thereof, which present greater surface area for tissue adhesion as well as promote despersion of forces during insertion. During the healing process, osteogenic activity will take place such that the bone structure is generated adjacent the blade portion of the implant in accordance with the contours thereof. The purpose for the openings 16 in the blade portion of the implant is to permit the bone to grow through the openings, thereby further enhancing the retention of the implant within the bone structure.

The head portion 18 of the implant may comprise a relatively massive multi-faceted body, generally tapered in a direction away from the neck portion 20 which serves as a physical and electrical connection to the blade portion 14. The head portion 18 is structured to facilitate the mounting of a false tooth thereon. However, this structure is also convenient for the connection of the negative lead of the output of the current generator B. This connection may be made by means of any releasable connector, such as an externally insulated alligator clip or the like.

The endodontic stabilizer, generally designated 22, as shown in FIG. 3, has an externally threaded portion 24 designed to be inserted through the root of the tooth with an aperture created in the jawbone for this purpose. The tip of portion 24 is inserted in the opening of the aperture and the stabilizer is rotated to imbed the stabilizer within the jawbone. The head portion 26 may extend into the oral cavity to receive a false tooth or the like for mounting thereon, or may subsequently be severed and removed leaving the remainder to stabilize the tooth. When osteogenic activity in the bone structure takes place, the bone will conform to the contours of the externally threaded portion 24 by growing between the threads to facilitate permanent retention thereof. The head portion 26 is provided with a flange-like protrusion 28 at the extreme end thereof. Flange portion 28 is spaced from the remainder of head 26 to provide an annular recess 30 such that connection with the lead from the output of current generator B can be made by means of a conductive spring-loaded hook or the like, which can be conveniently inserted into this annular recess.

Figure 4:
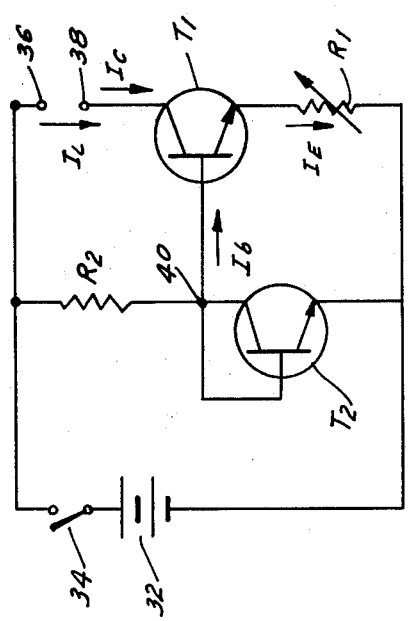
FIG. 4 is a schematic view of the pertinent portion of the circuitry of the direct current generator.

A schematic diagram of the basic portion of the direct current generator, including the means for retaining the output current level at a preset value, is illustrated in FIG. 4. The circuit comprises a voltage source 32 which is illustrated herein as a battery, but which may comprise any component capable of generating a constant voltage, such as a transformer-rectifier combination or the like. For the purposes of this description, voltage source 32 will be considered to supply a potential of 18 volts. However, it will be apparent to those skilled in the art that voltage sources of other values could be used with equal effectiveness providing the appropriate changes in the values of other components of the circuit are made accordingly.

In series with voltage source 32, is an on/off switch 34 which, when in the closed position, connects source 32 to the two portions of the current generating circuit which are connected in a parallel relationship. The first portion of the circuit comprises, in series, the circuit output nodes 36, 38, which are operably connected to implant 10 and the electrode 12, as indicated in FIG. 1, such that the implant acts as a cathode and the electrode acts as an anode; the output circuit of a transistor T1 and a variable resistor R1, preferably having a value of 50K. The resistance of resistor R1 can be varied to preset the magnitude of the current output.

The second portion of the circuit comprises a fixed resistor R2, preferably having a value of 100K, and the output circuit of a second transistor T2, which is connected thereto through a node 40. The base of each of the transistors T1 and T2 are also connected to node 40. The base of each of the transistors T1 and T2 are also connected to node 40.

When switch 34 is closed, source 32 energizes the circuit. The voltage (V) across resistor R1 is determined by the characteristics of transistor T2 and is, therefore, constant. This voltage is equal to the resistance R1 times the current through resistor R1. The current passing through resistor R1 is the emitter current ($I_E$) of transistor T1. The emitter current ($I_E$) is equal to the collector current ($I_C$) plus the base current ($I_B$). However, when transistor T1 is operated in the non-saturated mode, the base current ($I_B$) is negligible and, thus $I_E \approx I_C$. Therefore, $V \approx R1 \times I_C$.

The collector current ($I_C$) of transistor T1 is equal to the current ($I_L$) across the load connected between output nodes 36 and 38, which is the current path through the body of the subject. The voltage (V) across R1 is fixed, and the resistance of R1 is set, as indicated below. Thus, $I_E$ must be constant. Since $I_E \approx I_C = I_L$, then $V \approx R1 \times I_L$, or $I_L \approx V/R1$ and it is also constant. The load current ($I_L$) is thus independent of the magnitude of the load ($R_L$), namely, the resistance of the current path between the electrodes.

The resistance of R1 is set by initially monitoring the load current ($I_L$) by means of an ammeter and varying R1 until the desired load current ($I_L$) is obtained. Once this resistance is set, the circuit will maintain this current flow through the electrodes at this set value regardless of the resistance of the current path between the electrodes as long as the transistors are operated in the non-saturated mode. This is because $I_L$ is not a function of $R_L$, but only of V and R1. Variations in $R_L$ do not effect $I_L$.

Figure 5:
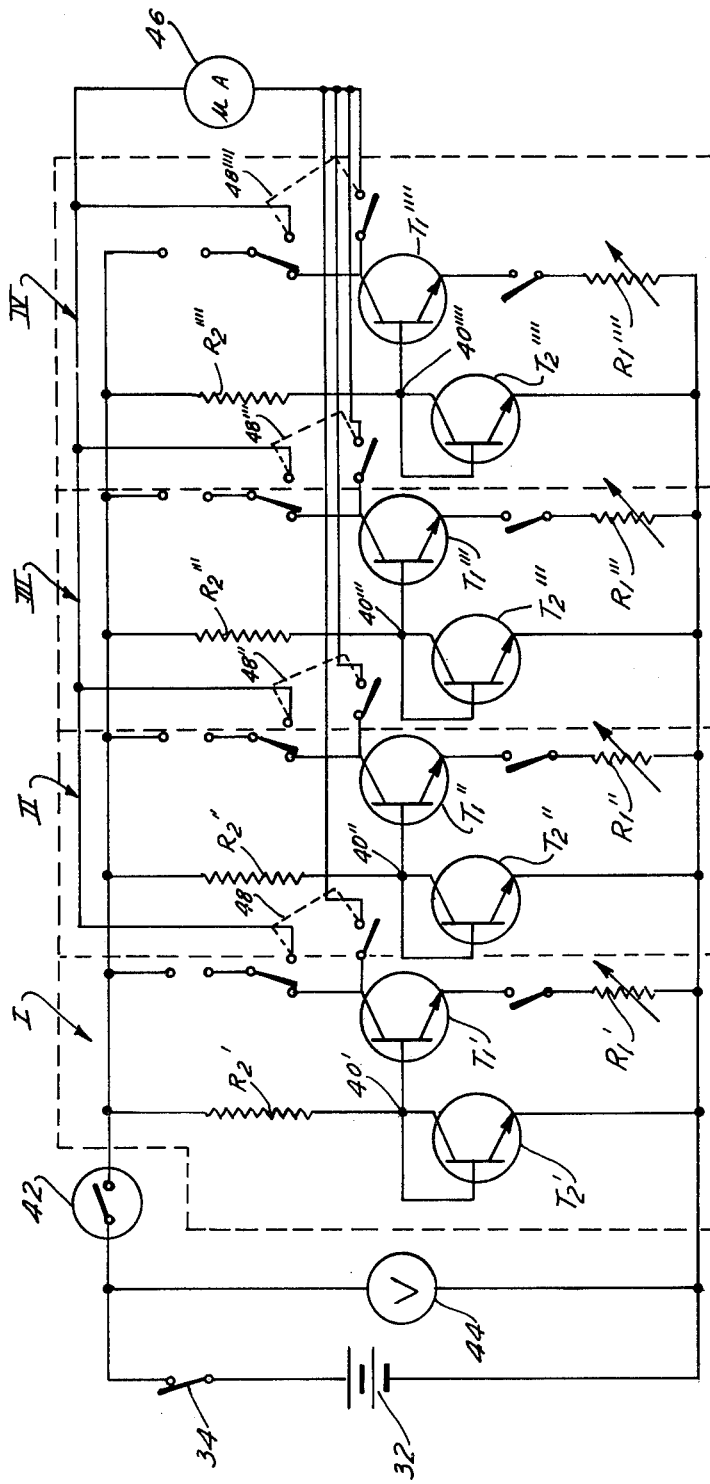
FIG. 5 is an overall schematic diagram of the direct current generator of the present invention.

The actual current generator utilized in the present invention is shown schematically in FIG. 5. This generator is formed of four different stages I, II, III and IV, respectively, each of which is essentially identical to the circuit shown in FIG. 4. Each of the stages is capable of generating a direct current of substantially constant magnitude at a preset value independent of electrical variations in the neighboring stages. The components of each of the four stages are identical in structure and function and, therefore, are labeled in correspondence with the components shown in FIG. 4, but with primes added thereto to indicate the stage in which they appear. Thus, all components with a single prime are within the I stage, a double prime within the II stage, etc.

The apparatus shown in FIG. 5 does, however, include some additional peripheral components. A timer 42 is connected in series with switch 34 such that the operator of the apparatus can set the apparatus to generate a current for a predetermined duration. Preferably, this duration will be of relatively short duration of up to approximately one hour in length, the treatment being given preferably three times a week. In addition, a volt meter 44 is included in the circuit so that a reading of the output of source 32 can easily be obtained. Further, a milliammeter 46 is connected to switches 48', 48'', 48''' and 48'''' so that by merely closing the appropriate switch, an accurate reading of the current across any selected output node can be ascertained in order to set the variable resistances, as indicated above.

The purpose for having four electrically independent current outputs is to permit the stimulation of osteogenic activity in up to four different sites within the mouth of one or more subjects simultaneously through the use of a single monitoring device. The apparatus is supplied with the appropriate metering devices to assist the operator in setting the current at each output, as well as the appropriate timing device to atuomatically terminate the treatment at the appropriate time.

Thus the present invention relates to a method and apparatus for stimulating osteogenic activity in retentive bone structure conforming to the contours of a dental implant. The method comprises the steps of permanently imbedding in the jawbone an electroconductive dental implant extending into the oral cavity. A non-permanently affixed second electrode is located on the body of the subject in the vicinity of the implant. A direct current is applied to the implant and the electrode, the implant acting as a cathode and the electrode acting as an anode. The current generating means preferably includes a means for controlling the applied current to maintain same at a substantially constant current level throughout the application thereof, regardless of the variations in the resistance value of the current path through the body of the subject. Preferably, the current is applied intermittently for periods of up to approximately one hour, preferably three times a week. Experimentation has indicated that a current of 200 microamperes or less is preferable, with satisfactory results being obtained at current levels of 100 microamperes, 40 microamperes and 20 microamperes respectively.

While only a single preferred embodiment of the present invention has been disclosed herein for purposes of illustration, it is obvious that many variations and modifications could be made thereto. It is intended to cover all of these variations and modifications which fall within the scope of the present invention as defined by the annexed claims.

We claim:

1. A method of stimulating osteogenic activity in bone structure adjacent to the contours of a dental implant comprising the steps of:
   a. permanently imbedding in the jawbone a first electrode comprising an electroconductive dental implant a portion of which extends into the oral cavity;
   b. non-permanently affixing a second electroconductive electrode on the body of the subject; and
   c. applying a direct current to said implant and said second electrode, said implant acting as a cathode and said second electrode acting as an anode.

2. The method of claim 1 further comprising the step of controlling the current to maintain a substantially constant current level throughout application thereof.

3. The method of claim 1 wherein the step of applying the direct current comprises the step of applying the direct current intermittently for given time periods.

4. The method of claim 3 wherein said given time periods are of relatively short duration of up to approximately one hour.

5. The method of claim 4 wherein the step of applying direct current comprises the step of applying direct current of 200 microamperes or less.

6. The method of claim 4 wherein said second electrode is affixed externally to the body of the subject on the skin.

7. The method of claim 3 wherein the step of applying direct current comprises the step of applying direct current of 200 microamperes or less.

8. The method of claim 3 wherein said second electrode is affixed externally to the body of the subject on the skin.

9. The method of claim 1 wherein the step of applying direct current comprises the step of applying direct current of 200 microamperes or less.

10. The method of claim 9 wherein said second electrode is affixed externally to the body of the subject on the skin.

11. The method of claim 1 wherein said second electrode is affixed to a part of the body of the subject outside the mouth.

12. The method of claim 1 wherein said second electrode is affixed externally to the body of the subject on the skin.

13. The method of claim 12 wherein said second electrode is affixed on the ear of the subject.

14. Apparatus for stimulating osteogenic activity in bone structure conforming to the contours of a dental implant comprising:
   a. an electroconductive dental implant having a first part which comprises means for allowing the dental implant to be permanently imbedded in the jawbone of a subject and a second part which comprises means for allowing the dental implant to extend into the oral cavity of the subject from the implantation site;
   b. an electrode adapted to be externally attached to the skin of the subject;
   c. means for generating a direct current;
   d. means for connecting the output circuit of said direct current generating means to said second part of the implant and said electrode, respectively, said implant being connected as a cathode and said electrode as an anode;
   e. said current generating means comprising means for maintaining the output of said current generating means at a substantially constant current level, independent of the resistance between said implant and said electrode.

15. The apparatus of claim 14 wherein said implant is of the blade type.

16. The apparatus of claim 15 wherein said blade is vented.

17. The apparatus of claim 14 wherein said implant is an endodontic stabilizer.

18. The apparatus of claim 14 wherein said implant is a pin implant of the threaded type.

19. The apparatus of claim 14 wherein said implant is a screw implant.

20. The apparatus of claim 14 wherein said first part is externally threaded.

21. The apparatus of claim 14 wherein said current generating means generates a current of 200 microamperes or less.

22. The apparatus of claim 14, wherein said current generating means comprises a power source, the circuit output and a variable resistor; said source, said circuit output and said variable resistor being operatively interconnected, and means operably connected to said resistor for maintaining the voltage across said resistor at a constant level, independent of the load across the circuit output.

23. The apparatus of claim 22 further comprising a first transistor, the output circuit of which is interposed between said circuit output and said resistor.

24. The apparatus of claim 23 wherein said voltage maintaining means comprises a second transistor, the output circuit of which is connected in parallel with said resistor.

25. The apparatus of claim 24 further comprising a fixed resistor connected in series with the output circuit of said second transistor through a node.

26. The apparatus of claim 25 wherein the control terminals of said first and second transistors are connected to said node.

27. The apparatus of claim 22, further comprising a plurality of independent direct current generating means, a plurality of implant and electrode pairs and means for independently connecting the output circuits of each of said generating means to said plurality of implant and electrode pairs, respectively.

28. The apparatus of claim 14 wherein said current generating means comprises: a power source, and first and second circuit portions, said second portion comprising said maintaining means, said first circuit portion comprising the circuit output, the output circuit of a first transistor and a variable resistance, said second circuit portion comprising a fixed resistance, a node and the output circuit of a second transistor, the control terminals of said first and second transistors being operably connected to said node, said first and second circuit portions being connected in parallel with each other, but in series with said source.

* * * * *